United States Patent [19]

Chupp et al.

[11] Patent Number: 5,587,485

[45] Date of Patent: Dec. 24, 1996

[54] HETEROCYCLIC- AND CARBOCYCLIC-SUBSTITUTED BENZOIC ACIDS AND SYNTHESIS THEREOF

[75] Inventors: John P. Chupp; Bruce C. Hamper, both of Kirkwood; Richard H. Wettach, Manchester, all of Mo.

[73] Assignee: Monsanto Company, St. Louis, Mo.

[21] Appl. No.: 407,352

[22] Filed: Mar. 20, 1995

Related U.S. Application Data

[62] Division of Ser. No. 277,726, Jul. 20, 1994, abandoned.

[51] Int. Cl.$^6$ ................. C07D 231/12; C07D 231/16; C07D 231/18
[52] U.S. Cl. ........................... 548/377.1; 548/366.1
[58] Field of Search ................. 548/206, 377.1, 548/366.1

[56] References Cited

U.S. PATENT DOCUMENTS 4,160,108  7/1979  Shigeyasu et al. ................. 562/416
5,053,517  10/1991  Takigawa et al. ................. 548/376

FOREIGN PATENT DOCUMENTS

WO92/06962  10/1991  WIPO ................. C07D 231/16
9400407  1/1994  WIPO .

OTHER PUBLICATIONS

Morrison et al., Organic Chemistry, 5th ed., Allyn and Bacon Inc., (1959).

*Primary Examiner*—Joseph McKane
*Assistant Examiner*—Laura R. Cross
*Attorney, Agent, or Firm*—Joan Thierstein; Arnold, White & Durkee

[57] ABSTRACT

The disclosure herein relates to the title compounds and synthesis thereof by catalytic oxidation of the corresponding alkyl-substituted phenylheterocyclic or carboxylic compound.

9 Claims, No Drawings

HETEROCYCLIC- AND CARBOCYCLIC-SUBSTITUTED BENZOIC ACIDS AND SYNTHESIS THEREOF

This is a Divisional of application Ser. No. 08/277,726, filed on Jul. 20, 1994, now abandoned.

FIELD OF THE INVENTION

The present invention relates to a class of heterocyclic and carbocyclic-substituted benzoic acids and processes for their preparation from corresponding methylphenylheterocyclic and carbocyclic compounds. Benzoic acids of this type obtained by direct oxidation with molecular oxygen are useful as intermediates in the preparation of agricultural compounds and medicines, particularly as intermediates for an active class of aryl-haloalkylpyrazole and aryl alkylsulfonylpyrazole herbicides.

BACKGROUND OF THE INVENTION

It is known in the prior art to produce a variety of oxygenated derivatives of aliphatically-substituted aromatic compounds by oxidation of the aliphatic substituent(s). For example, mono- and polynuclear aromatic compounds such as benzene, diphenyl, naphthalene, anthracene, phenanthrene, etc., having one or more mono- or bifunctional aliphatic groups, may be partially oxidized to derivatives such as alcohols, aldehydes, ketones, peroxides, etc. Mono- and polycarboxylic aromatic acids are also produced by oxygenation of the corresponding aliphatic substituted aromatic compound.

Oxidation processes of the above type are disclosed in U.S. Pat. No. 2,833,816 and Japanese Laid-Open Patent Application (Kokai) No.1 59-27850, wherein aromatic hydrocarbons containing only $C_{1-4}$ alkyl groups and/or halogens substituted thereon are oxidized to corresponding oxygenated derivatives by the liquid-phase reaction of the aromatic hydrocarbon substrate with molecular oxygen in the presence of combination catalyst comprising bromine and a heavy metal oxidation catalyst. In addition, it is known (U.S. Pat. No. 5,053,517) to convert methylpyrazoles containing a variety of substituents to pyrazole carboxylic acids by liquid-phase reaction with molecular oxygen and suitable metal-salt catalysts.

Other prior art oxidation processes and their acid products relate to relatively new substituted phenylpyrazoles, which are useful as intermediates in the production of other derivatives which are herbicidally effective in agronomically important crops. Of particular note are certain substituted 3-aryl-5-substituted pyrazole compounds. Examples of such herbicidal compounds are disclosed in U.S. Pat. No. 5,032,165, wherein the chief characteristic feature in the 3-aryl-5-pyrazole compound is the substitution of an —$AR^5$ group on the 5-position of the pyrazole radical, wherein A is O or S and $R^5$ is hydrogen or lower (halo) alkyl. An earlier published counterpart of the U.S. Pat. No. '165 patent is EP Application No. EP 0361114, published Apr. 4, 1990. Another process for preparation of these compounds is disclosed in Japanese application No. 06073015-A.

The substituted 3-aryl-5-AR pyrazole compounds in said U.S. Pat. No. '165 patent and EP '114 application are produced by a multi-step procedure involving: (1) halogenation of a methyl group in the 5 position of a 3-phenyl-5-$AR^5$ pyrazole substrate to form the corresponding 5-halomethyl compound; (2) reacting the latter with an arylamine and formaldehyde in hexamine (i.e., the Sommelet reaction) followed by acid hydrolysis to substitute a formaldehyde group for the halomethyl radical in the 5-position of the phenyl radical and (3) oxidizing said formaldehyde group to a carboxylic acid radical. The resulting compound is useful as an intermediate to form the final product having on the phenyl ring a 5-ester group by esterification of the 5-COOH group with an alcohol.

Other 3-aryl-5-substituted pyrazole compounds having improved herbicidal efficacy are disclosed in related application Ser. No. 07/763,762, now U.S. Pat. No. 5,281,571, a continuation-in-part of Ser. No. 07/600,031, now abandoned, and in South African Patent No. 6,197 (counterpart of U.S. Ser. No. 07/735,091, now abandoned). In said U.S. Pat. No. '571 patent, the compounds are characterized by having a haloalkyl substituent in the 5-position of the pyrazole group, while in said South African Patent No. 6,197, the 5-position of the pyrazole group is substituted with an alkylsulfonyl radical. The compounds in the foregoing patents are prepared in a multi-step process in order to obtain the benzoic acid radical.

The prior art does not disclose methods for the direct oxidation of aryl compounds having as substituents thereon both alkyl group(s) and, additionally, a carbocyclic or heterocyclic group—as exemplified above, wherein multi-step processes are required to form the precursor aryl acid, which is used to form the final ester.

It is, therefore, an object of this invention to provide novel benzoic acid-carbocyclic and 3-benzoic acid-substituted heterocyclic compounds, e.g., 5[substituted pyrazole]-halo-(un)substituted benzoic acids useful as intermediates or precursors to produce the corresponding ester compounds which are useful herbicidal compounds.

It is a further object of this invention to provide a novel process for the direct oxidation of aryl compounds substituted with alkyl (preferably $C_{1-4}$) groups and with carbocyclic or heterocyclic groups to produce the corresponding aryl acid/carbocyclic or heterocyclic compounds.

A particular object of this invention is the provision of novel 5[substituted pyrazol]-halo-substituted benzoic acids and a method for the direct oxidation of the corresponding alkyl-substituted precursor compound.

A special object of this invention is to provide the novel compound 5-[4-bromo-1-methyl-5-(trifluoromethyl)-1H-pyrazol-3-yl)-2-chloro-4-fluorobenzoic acid and its synthesis by direct oxidation of the corresponding alkylphenylpyrazole. Esters of said benzoic acid, especially the isopropyl ester, are also provided by esterification of said acid.

SUMMARY OF THE INVENTION

In one aspect, the present invention relates to novel benzoic acid derivatives of Formula I

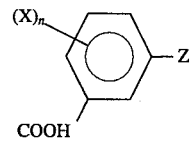

and salts and esters thereof wherein

X is halogen, $C_{1-6}$ polyhaloalkyl, $C_{6-10}$ aryloxy, $C_{1-6}$ alkoxy or alkylsulfonyl, $C_{4-10}$ tert-alkyl, $NO_2$ or CN, $C_{1-6}$(halo)alkyl or alkylthio; alkoxyalkyl or polyalkoxy having up to 8 carbons atoms; (halo)alkenyl or (halo)alkynyl having up to 6 carbon atoms; $NH_2$, CHO or COAR, where A is O or S and R is a (halo)alkyl, (halo)alkenyl, or (halo)alkynyl group having up to 6 carbon atoms;

n is 0–4 and

Z is an (un)substituted carbocyclic or heterocyclic ring having up to 8 ring members, said heterocyclic ring containing one or more O, N or S atom(s), in which the ring carbon substituents may be one or more X members and substituents on ring N heteroatoms may be $C_{1-6}$ (halo)alkyl, hydrogen or an X member.

Preferred compounds according to Formula I are those wherein the Xs are halogen and Z is a substituted 3- or 5-pyrazolyl radical.

More preferred compounds of Formula I are those within a subclass of benzoic acid pyrazoles according to Formula II

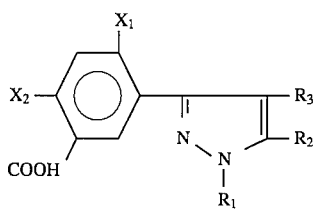

II and salts and esters thereof wherein $X_1$ and $X_2$ are halogen or hydrogen;

$R_1$ is $C_{1-6}$ alkyl;

$R_2$ is $C_{1-6}$ haloalkyl or alkylsulfonyl and $R_3$ is H or halogen.

Still more preferred compounds according to Formula II are those wherein $X_1$ is fluorine;

$X_2$ is chlorine or bromine;

$R_1$ is methyl;

$R_2$ is —$CF_3$, —$CF_2Cl$, $C_2F_5$ or —$CF_2H$;

$R_3$ is hydrogen, bromine or chlorine.

Preferred species of compounds according to Formula II are:

5-[4-chloro-1-methyl-5-(trifluoromethyl)-1H-pyrazol-3-yl]-2-chloro-4-fluorobenzoic acid;

5-[4-bromo-1-methyl-5-(trifluoromethyl)-1H-pyrazol-3-yl]-2-chloro-4-fluorobenzoic acid;

5-[4-chloro-1-methyl-5-(trifluoromethyl)-1H-pyrazol-3-yl]-2-chloro-4-fluorobenzoic acid, n-propyl ester;

5-[4-chloro-1-methyl-5-(trifluoromethyl)-1H-pyrazol-3-yl]-2-chloro-4-fluorobenzoic acid, i-propyl ester;

5-[4-bromo-1-methyl-5-(trifluoromethyl)-1H-pyrazol-3-yl]-2-chloro-4-fluorobenzoic acid, n-propyl ester and 5-[4-bromo-1-methyl-5-(trifluoromethyl)-1H-pyrazol-3-yl]-2-chloro-4-fluorobenzoic acid, i-propyl ester.

In another aspect, this invention relates to a novel process for the production of compounds according to Formulae I and II, which comprises the direct oxidation of compounds according to Formula III

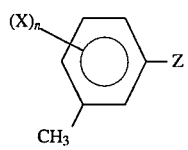

III wherein X, n and Z are as previously defined. In preferred embodiments, a compound according to Formula III wherein both Xs in the ortho and para positions are halogen and Z is a 3- or 5-pyrazolyl compound and is oxidized in the liquid phase with molecular oxygen or a gas containing oxygen in the presence of an oxidation catalyst. Reaction temperatures range from about 0° C.–300° C. and pressures within the range of sub-ambient to <70.3 kg/cm².

DETAILED DESCRIPTION OF THE INVENTION

The pyrazolylbenzoic acids herein are prepared from methylphenylpyrazoles by oxidation with molecular oxygen in a suitable solvent in the presence of catalyst or mixture of catalysts and other adjuvants at a temperature range of 0° C. to 300° C., preferably 50° C. to 150° C. Any suitable solvent which does not interfere with the course of the reaction may be employed, with acetic acid being preferred. The oxygen source may consist of pure oxygen, air or mixture of oxygen or air in other carriers. Reaction rate can be favorably influenced by application of pressure and any pressure from about 1.0–<70.3 kg/cm² (one atmosphere to greater than 1000 psi) can be employed depending on the equipment and the desired rate of reaction. The use of pressures above one kg/cm² has a favorable impact on reaction rates; however, this does not exclude the use of higher or lower pressures.

Catalysts or mixture of catalysts and adjuvants are used to favorably effect the rate of oxidation. Metal salt catalyst mixtures containing any single or combination of salts may be used including, but not limited to, cobalt salts, manganese salts, nickel salts, cesium salts and zirconium salts. Examples of such salts are the aliphatic acid salts, cobalt (II) acetate, cobalt formate, cobalt hexylate, manganese (II) acetate, cesium (III) acetate, etc., chelate compounds such as cobalt acetylacetonate, zirconium (IV) acetylacetonate, etc., and metal salts such as cobalt chloride, cobalt carbonate, nickel chloride, manganese chloride, zirconium chloride, etc. Other catalysts include alkali halides, alkyl halide, lithium salts, bromide salts, carboxylate slats, etc., including, but not limited to, hydrogen bromide, sodium bromide, bromoacetic acid, ammonium bromide, sodium acetate, etc. The amount of catalyst or each catalyst of a mixture can range independently from less than 1 mole % to nearly one molar equivalent relative to the compound of Formula III.

Intermediate halogenated or oxidized compounds obtained from derivitization of a compound of Formula III can also be employed as adjuvants. Thus the benzyl bromide derivatives obtained by bromination of the methylphenyl group or the benzaldehydes obtained by partial oxidation of the methylphenyl group can be added to the reaction mixture to favorably enhance reaction rates. Peroxides, such as hydrogen peroxide, can also be used to initiate or reinitiate the oxidation and are particularly convenient for initiation or reinitiations of atmospheric pressure oxidations especially if the oxidation slows prior to completion. The amounts of adjuvants is not particularly limited and can be employed in whatever quantities necessary to obtain desired reaction rates. Preferred amounts of single adjuvants or mixtures of adjuvants are, independently, from less than 0.1 mole % to 10 mole %.

Any suitable solvent can be employed which is stable to the reaction conditions or the reaction can be carried out in the absence of solvent. Preferred solvents include, but are not limited to, aliphatic carboxylic acids and anhydrides such as acetic acid and acetic anhydride. The amount of solvent employed is not particularly limited, however, reaction rates are enhanced by the use of a limited amount of solvent.

Overall yields and ease of process manipulation can be favorably improved by combining the steps for halogenation and oxidation as exemplified below in the case of a methylphenyl-4-hydropyrazole of Formula IV to a 4-halopyrazolylbenzoic acid (Formula II compound wherein $R_3$ is halogen) as one step without isolation of an intermediate. The two reaction steps in this process can be carried out in either of two possible orders; halogenation followed by oxidation or oxidation followed by halogenation. The preferred sequence is oxidation followed by halogenation.

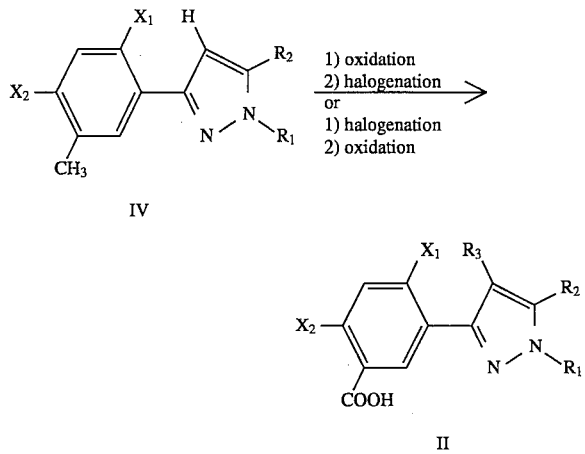

The compounds of Formula II obtained by this process are particularly useful for the preparation of arylpyrazole herbicides as has been previously described. The carboxylic acid group can be derivatized to prepare a variety of herbicidal ester, amide, thioester, thioamide, etc., derivatives by methods known in the art. For example, suitable alcohols, e.g., propyl or isopropyl alcohol may be used to esterify the COOH group as exemplified in Example 6 below.

The following Examples 1–6 describe specific working embodiments for the preparation of representative compounds according to this invention.

Examples 1 to 3 describe specific working embodiments of the single step oxidation of compounds of Formula IV.

EXAMPLE 1

Preparation of 2-Chloro-5-[4-chloro-1-methyl-5-(trifluoromethyl)-1H-pyrazol-3-yl]-4-fluorobenzoic acid. (Compound No. 1)

A solution of 700 g (2.14 mol) 4-chloro-3-(4-chloro-2-fluoro-5-methylphenyl)-1-methyl-5-(trifluoromethyl)-1H-pyrazole in 1000 mL of glacial acetic acid was prepared in a 5 L round bottom flask and treated with a catalyst mixture consisting of 5.25 g cobaltous acetate tetrahydrate, 0.55 g manganous acetate tetrahydrate and 4.2 g of sodium bromide. The flask contents was heated to 95° C. and an air stream (20.9% oxygen) was introduced into the stirred reaction mixture. After heating for two days, the mixture was treated with 2.5 L cold water, allowed to cool to room temperature. The resultant solid was collected by filtration and air dried to yield 745 g (97.4%) of a white solid. An analytical sample was recrystallized from ether/hexanes: mp 179° C.–181° C.; $^1$H NMR (CDCl$_3$+DMSO) δ 11.84 (s, broad, 1H), 8.09 (d, J=8 Hz, 1H), 7.21 (d, J=10 Hz, 1H), 3.96 (s, 3H); $^{19}$F NMR (CDCl$_3$+DMSO) δ −63.9 (s, 3F), −110.4 (m, 1F).

Anal. Calc. for $C_{13}H_6N_2O_2F_4Cl_2$: C,40.36; H,1.69; N,7.84. Found: C,40.49; H,1.74; N,7.77.

EXAMPLE 2

Preparation of 2-Chloro-5-[1-methyl-5-(trifluoromethyl)-1H-pyrazol-3-yl]-4-fluorobenzoic acid. (Compound No. 2)

A mixture of 40.6 g 3-(4-chloro-2-fluoro-5-methylphenyl)-1-methyl-5-(trifluoromethyl)-1H-pyrazole in 70 mL of glacial acetic acid with 0.34 g of Cobalt (II) acetate tetrahydrate, 0.033 g manganese (II) acetate tetrahydrate, 0.28 g sodium bromide and 0.1 g was placed in a 300 mL Parr Hastaloy C autoclave equipped with stirring and pressurized to 7.0 Kg/cm$^2$ with oxygen gas. The vessel was heated to 145° C. and the oxygen pressure maintained at 10.5 Kg/cm$^2$ by addition of more oxygen. After uptake of oxygen had subsided (203 hrs.), the mixture was maintained at 145° C.–150° C./10.5 kg/cm$^2$ (150 psi) for an additional 90 minutes. The autoclave was allowed to cool, depressurized and the contents added to 400 mL of cold water. The slurry was filtered, the solid washed with cold water and air dried to yield 42.2 g (94.3%) of a white solid. An analytical sample was obtained by recrystallization from ethyl acetate: mp 195° C.–197° C.; $^1$H NMR (CDCl$_3$) δ 4.01 (s, 3H), 6.93 (s, 1H), 7.18 (d, 1H), 8.67 (d, 1H).

Anal. Calcd. for $C_{12}H_7ClF_4N_2O_2$: C, 44.67; H, 2.19; N, 8.68. Found: C,44.67; H,2.18; N,8.63.

EXAMPLE 3

Preparation of 2-Chloro-5-[1-methyl-5-(trifluoromethyl)-1H-pyrazol-3-yl]-4-fluorobenzoic acid. (Compound No. 2)

A solution of 100 g (0.34 mol) 3-(4-chloro-2-fluoro-5-methylphenyl)-1-methyl-5-(trifluoromethyl)-1H-pyrazole in 400 mL of glacial acetic acid was prepared in a 1 L Morton type flask and treated with a catalyst mixture consisting of 0.85 g cobaltous acetate tetrahydrate, 0.10 g manganous acetate tetrahydrate and 1.05 g of sodium bromide. The flask contents was heated to 109° C. and an air stream (20.9% oxygen) was introduced at a flow rate of 150 mL/min. into the stirred reaction mixture. Five drops of 50% hydrogen peroxide was added to initiate the reaction. As the reaction ensued, the oxygen in the air stream exiting from the reaction mixture dropped from 20.9% to 8.9%. After 22 hours, the mixture was treated with 750 mL cold water and allowed to cool to room temperature. The resultant solid was collected by filtration, washed with 1 L of cold water and air dried to yield 104 g (97.4%) of a tan-white solid. An analytical sample was recrystallized from ethyl acetate: mp 195° C.–197° C.

Examples 4 and 5 describe specific working embodiments of the combined oxidation-halogenation sequence to give compounds of Formula II wherein R$_3$ in halogen.

EXAMPLE 4

Preparation of 2-Chloro-5-[4-chloro-1-methyl-5-(trifluoromethyl)-1H-pyrazol-3-yl]-4-fluorobenzoic acid. (Compound No. 1)

A solution of 100 g (0.34 mol) 3-(4-chloro-2-fluoro-5-methylphenyl)-1-methyl-5-(trifluoromethyl)-1H-pyrazole in 400 mL of glacial acetic acid was prepared in a 1 L Morton type flask and treated with a catalyst mixture consisting of 0.85 g cobaltous acetate tetrahydrate, 0.10 g manganous acetate tetrahydrate and 1.65 g of sodium bromide. The flask contents was heated to 105° C. and an air stream (20.9% oxygen) was introduced at a flow rate of 150 mL/min. into the stirred reaction mixture. Five drops of 50% hydrogen peroxide was added to initiate the reaction. After 24 hours, the mixture was allowed to cool to room temperature, resulting in a slurry containing the benzoic acid (Compound No. 2). To the stirred slurry was added 25.5 g (0.34 mol) chlorine gas over a period of 10 minutes. The mixture was kept at 30° C. overnight and subsequently treated with 700 mL of cold water. Filtration of the slurry gave a solid which was washed thrice with 500 mL water and allowed to air dry to give 114 g (93.7%) of a white solid: mp 179° C.–181° C.

EXAMPLE 5

Preparation of 5-[4-Bromo-1-methyl-5-(trifluoromethyl)-1H-pyrazol-3-yl]-2-chloro-4-fluorobenzoic acid. (Compound No. 3)

A solution of 100 g (0.34 mol) 3-(4-chloro-2-fluoro-5-methylphenyl)-1-methyl-5-(trifluoromethyl)-1H-pyrazole in 400 mL of glacial acetic acid was prepared in a 1 L Morton type flask and treated with a catalyst mixture consisting of 0.85 g cobaltous acetate tetrahydrate, 0.10 g manganous acetate tetrahydrate and 1.65 g of sodium bromide. The flask contents was heated to 105° C. and an air stream (20.9% oxygen) was introduced at a flow rate of 150 mL/min. into the stirred reaction mixture. Five drops of 50% hydrogen peroxide was added to initiate the reaction. After 24 hours, the mixture was allowed to cool to 50° C., resulting in a slurry containing the benzoic acid (Compound No. 2). To the stirred slurry was added 100 g (0.63 mol) bromine and the mixture heated to 65° C. After 6 hours, the mixture was treated with 25 mL of water and after 12 hours an additional 25 mL of water and 3.5 g of bromine was added. After a total reaction time of 24 hours, the mixture was treated with 185 mL of 23% sodium sulfite solution to destroy excess bromine. The resultant mixture was treated with 150 mL of ice to bring the temperature to 26° C. Filtration of the slurry gave a solid which was washed with cold water and the solid air dried to give 127.9 g (93.3%) of a white powder: mp 171° C.–173° C.; $^1$H NMR (CDCl$_3$) δ 4.22 (s, 3H), 7.49 (d, 1H), 8.39 (d, 1H).

Anal. Calcd. for $C_{12}H_6BrClF_4N_2O_2$: C,35.87; H,1.50; N,6.97. Found: C,35.79; H,1.63; N,6.90.

Example 6 describes a specific working embodiment of the conversion of a compound of Formula II to an arylpyrazole derivative.

EXAMPLE 6

Preparation of 1-Methylethyl 5-[4-bromo-1-methyl-5-(trifluoromethyl)-1H-pyrazol-3-yl]-2-chloro-4-fluorobenzoate.

A solution of 100 g (0.25 mol) 5-[4-bromo-1-methyl-5-(trifluoromethyl)-1H-pyrazol-3-yl]-2-chloro-4-fluorobenzoic acid (Compound No. 3) in 580 mL of toluene was prepared and treated with 1 g of dimethylformamide (DMF). The stirred mixture was heated to 45° C., treated with 30 g (0.252 mol) of thionyl chloride and subsequently heated to 60° C.–65° C. for one hour. After cooling to 40° C., a solution of 30 g (0.50 mol) of isopropanol and 27.6 g (0.35 mol) pyridine was added at once. The mixture was stirred and heated to about 55° C. for 30 minutes to complete conversion of the intermediate acid chloride to the desired product. Treatment with 650 mL water and 45 g of acetone gave two clear layers. The aqueous layer was removed and the organic portion washed with water, saturated brine, dried with MgSO$_4$ and concentrated to give a viscous oil. A solid was obtained by solution of the oil into 250 g of warm isopropanol, cooling of the mixture to room temperature and slow treatment with 600 mL of cold water. The resultant precipitate was collected by filtration, washed with water and air dried to give 105 g (94.7%) of a white solid: mp 79.5° C.–80.5° C.; $^1$H NMR (CDCl$_3$) δ 1.49 (d, 6H), 4.21 (s, 3H), 5.38 (m, 1H), 7.43 (d, 1H), 8.14 (d, 1H).

Anal. Calcd for $C_{15}H_{12}BrClF_4N_2O_2$: C, 40.59; H, 2.71; N, 6.31. Found: C, 40.60; H, 2.73; N, 6.29.

The table below shows examples of Compounds of Formula II prepared by the above processes.

TABLE

PHYSICAL DATA FOR 5-PYRAZOL-3-YL BENZOIC ACIDS

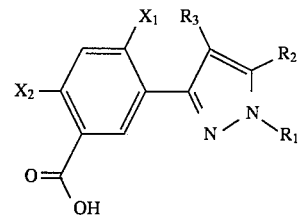

| Compound No. | $X_1$ | $X_2$ | $R_1$ | $R_2$ | $R_3$ | mp °C. |
|---|---|---|---|---|---|---|
| 1 | F | Cl | CH$_3$ | CF$_3$ | Cl | 179–180 |
| 2 | F | Cl | CH$_3$ | CF$_3$ | H | 195–197 |
| 3 | F | Cl | CH$_3$ | CF$_3$ | Br | 171–173 |
| 4 | F | Cl | CH$_3$ | SO$_2$CH$_3$ | Cl | 194–196 |
| 5 | F | Cl | CH$_3$ | CF$_2$Cl | Cl | 141.5–143.5 |
| 6 | Cl | Cl | CH$_3$ | CF$_3$ | Cl | 165 |
| 7 | H | Cl | CH$_3$ | CF$_3$ | Cl | 201 |
| 8 | H | H | CH$_3$ | CF$_3$ | Cl | 171–173 |
| 9 | F | Cl | CH$_3$ | SO$_2$CH$_3$ | Cl | 220–221 |
| 10 | Cl | F | CH$_3$ | CF$_3$ | H | 184–186 |
| 11 | F | F | CH$_3$ | CF$_3$ | H | 194–195 |
| 12 | F | Cl | CH$_3$ | CF$_3$ | CO$_2$H | 262 |
| 13 | Cl | F | CH$_3$ | CF$_3$ | Cl | 168–170 |
| 14 | Cl | F | CH$_3$ | CF$_3$ | Br | 179.5–182.0 |
| 15 | F | F | CH$_3$ | CF$_3$ | Cl | 157–159 |
| 16 | F | Br | CH$_3$ | CF$_3$ | H | 193–195 |
| 17 | F | Br | CH$_3$ | CF$_3$ | Cl | 166.4–168.5 |
| 18 | F | Br | CH$_3$ | CF$_3$ | Br | 174–176 |
| 19 | F | Cl | H | CF$_3$ | H | 250 |
| 20 | F | Cl | H | CF$_3$ | Br | 240 |

The heterocyclic- or carbocyclic-substituted benzoic acids of the present invention are useful as intermediates for the preparation or manufacture of agricultural chemicals and medicines, particularly for preparation of substituted phenylpyrazole type herbicides. This process allows the direct introduction of the benzoic acid functionality in the 5'-position of the phenyl ring of the arylpyrazole which can be converted to ester and amide derivatives. In addition, both the halogenation of the heterocyclic ring and the oxidation of the methyl group on the phenyl ring can be carried out as a one step procedure, eliminating isolation of an intermediate.

Various equivalent modifications of this invention described herein will occur to those skilled in the art.

We claim:

1. Process for the preparation of compounds according to Formula I

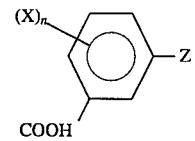

and salts and esters thereof wherein

X is halogen $C_{1-6}$ (halo)alkyl, or alkylsulfonyl; alkoxyalkyl or polyalkoxy having up to 8 carbon atoms; (halo)alkenyl or (halo)alkynyl having up to 6 carbon atoms; NH$_2$, NO$_2$, CN, or COAR, where A is O or S and R is a (halo)alkyl, (halo)alkenyl, or (halo)alkynyl group having up to 6 carbon atoms;

n is 0–4 and

Z is a pyrazole ring having at least one substituent which is a $C_{1-6}$ alkyl group; the other ring substituent(s), if any, which ring substituents may be one or more X members, which comprises oxidizing a compound according to Formula III

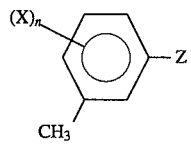

III wherein X, n and Z are as previously defined; with oxygen or an oxygen-containing gas in the presence of an oxidizing catalyst in an inert solvent.

2. Process according to claim 1 wherein the oxidation reaction is conducted at temperatures within the range of about 0° C.–300° C. and pressures within the range of sub-ambient to <70.3 kg/cm$^2$.

3. Process according to claim 2 wherein said catalyst is one or more metal salts.

4. Process according to claim 1 wherein said compound of Formula I is within a subclass of compounds according to Formula II

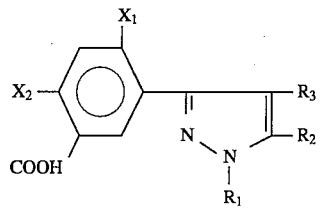

II and salts and esters thereof wherein $X_1$ and $X_2$ are halogen or hydrogen;

$R_1$ is $C_{1-6}$ alkyl;

$R_2$ is $C_{1-6}$ haloalkyl or alkylsulfonyl and $R_3$ is H or halogen.

5. Process according to claim 4 wherein in said Formula II $X_1$ is fluorine;

$X_2$ is chlorine;

$R_1$ is methyl;

$R_2$ is —$CF_3$, —$CF_2Cl$, —$C_2F_5$ or —$CF_2H$ and $R_3$ is H, bromine or chlorine.

6. Process according to claim 5 wherein said compound according to Formula II is selected from the group consisting of 5-[4-Chloro-1-methyl-5-(trifluoromethyl)-1H-pyrazol-3-yl]-2-chloro-4-fluorobenzoic acid and the n- and isopropyl esters thereof.

7. Process according to claim 5 wherein said compound according to Formula II is selected from the group consisting of 5-[4-Bromo-1-methyl-5-(trifluoromethyl)-1H-pyrazol-3-yl]-2-chloro-4-fluorobenzoic acid and the n- and isopropyl esters thereof.

8. Process according to claim 1 wherein in the compound according to Formula III, n is and at least one X group is a halogen.

9. Process according to claim 8 wherein the two X groups are independently selected from the halogens.

* * * * *

UNITED STATES PATENT AND TRADEMARK OFFICE
CERTIFICATE OF CORRECTION

PATENT NO. : 5,587,485

DATED : December 24, 1996

INVENTOR(S) : Chupp et al.

It is certified that error appears in the above-identified patent and that said Letters Patent is hereby corrected as shown below:

Column 3, line 67: "<" should read -->--

Column 4, line 13: "<" should read -->--

Column 8, line 62: insert "," after -- halogen --

Column 9, line 20: "<" should read -->--

Column 10, line 29: after "n is" insert --2--

Signed and Sealed this

Sixth Day of May, 1997

*Attest:*

BRUCE LEHMAN

*Attesting Officer*  *Commissioner of Patents and Trademarks*